United States Patent
Bai et al.

(10) Patent No.: US 11,510,641 B2
(45) Date of Patent: Nov. 29, 2022

(54) NON-SPECTRAL COMPUTED TOMOGRAPHY (CT) SCANNER CONFIGURED TO GENERATE SPECTRAL VOLUMETRIC IMAGE DATA

(71) Applicant: KONINKLIJKE PHILIPS N.V., Eindhoven (NL)

(72) Inventors: Chuanyong Bai, Solon, OH (US); Yang-Ming Zhu, Willimgton, MA (US); Sheng Lu, Highland Heights, OH (US); Shiyu Xu, Mayfield Heights, OH (US); Hao Dang, Mayfield Heights, OH (US); Hao Lai, Rexford, NY (US); Douglas B. McKnight, Chardon, OH (US); Hui Wang, Beachwood, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 16/965,201

(22) PCT Filed: Jan. 30, 2019

(86) PCT No.: PCT/EP2019/052271
§ 371 (c)(1),
(2) Date: Jul. 27, 2020

(87) PCT Pub. No.: WO2019/149762
PCT Pub. Date: Aug. 8, 2019

(65) Prior Publication Data
US 2021/0059625 A1    Mar. 4, 2021

Related U.S. Application Data

(60) Provisional application No. 62/624,431, filed on Jan. 31, 2018.

(51) Int. Cl.
*A61B 6/00*    (2006.01)
*G16H 30/40*   (2018.01)
(Continued)

(52) U.S. Cl.
CPC .............. *A61B 6/52* (2013.01); *A61B 6/032* (2013.01); *G06N 3/08* (2013.01); *G16H 30/40* (2018.01); *A61B 6/483* (2013.01)

(58) Field of Classification Search
CPC .................................................... A61B 6/482
See application file for complete search history.

(56) References Cited

U.S. PATENT DOCUMENTS 7,968,853 B2   6/2011   Altman
8,442,184 B2   5/2013   Forthmann
(Continued)

FOREIGN PATENT DOCUMENTS

WO   WO2016042491 A1   3/2016
WO   WO2017223560 A1   12/2017

OTHER PUBLICATIONS

PCT International Search Report, International application No. PCT/EP2019/052271, dated May 14, 2019.
(Continued)

*Primary Examiner* — Dani Fox
(74) *Attorney, Agent, or Firm* — Larry Liberchuk

(57) ABSTRACT

A non-spectral computed tomography scanner (102) includes a radiation source (112) configured to emit x-ray radiation, a detector array (114) configured to detect x-ray radiation and generate non-spectral data, and a memory (134) configured to store a spectral image module (130) that includes computer executable instructions including a neural network trained to produce spectral volumetric image data. The neural network is trained with training spectral volumetric image data and training non-spectral data. The non-
(Continued)

spectral computed tomography scanner further includes a processor (126) configured to process the non-spectral data with the trained neural network to produce spectral volumetric image data.

19 Claims, 5 Drawing Sheets

(51) Int. Cl.
 *A61B 6/03* (2006.01)
 *G06N 3/08* (2006.01)

(56) References Cited

U.S. PATENT DOCUMENTS

2015/0201895 A1 7/2015 Suzuki
2015/0371378 A1 12/2015 Schmidt

OTHER PUBLICATIONS

Chen H. et al., "Deep Learning for Low-Dose CT", Proceedings of SPIE 10391, Developments in X-Ray Tomography XI, Sep. 2017.
Li S. et al., "Pseudo Dual Energy CT Imaging Using Deep Learning Based Framework: Initial Study", Medical Physics arXiv., Nov. 2017.
Zhang H. et al., "Reconstruction of Limited-Angle Dual-Energy CT Using Mutual Learning and Cross-Estimation (MLCE)", Proceedings of SPIE, vol. 9783, Medical Imaging 2016: Physics of Medical Imaging, 978344, Mar. 30, 2016.
Gouk H.G.R. et al., "Fast Sliding Window Classification with Convolutional Neural Networks," IVNVZ '14 Proceedings of the 29th International Conference on Image and Vision Computing New Zealand, pp. 114-118, Nov. 19-21, 2014.
Long J. et al., "Fully Convolutional Networks for Semantic Segmentation." Proceedings of the IEEE Conference on Computer Vision and Pattern Recognition (CVPR), 2015, pp. 3431-3440.
Ronneberger O. et al., "U-Net: Convolutional Networks for Biomedical Image Segmentation", Medical Image Computing and Computer-Assisted Intervention (MICCAI), Springer, LNCS, vol. 9351: 234-241,2015.

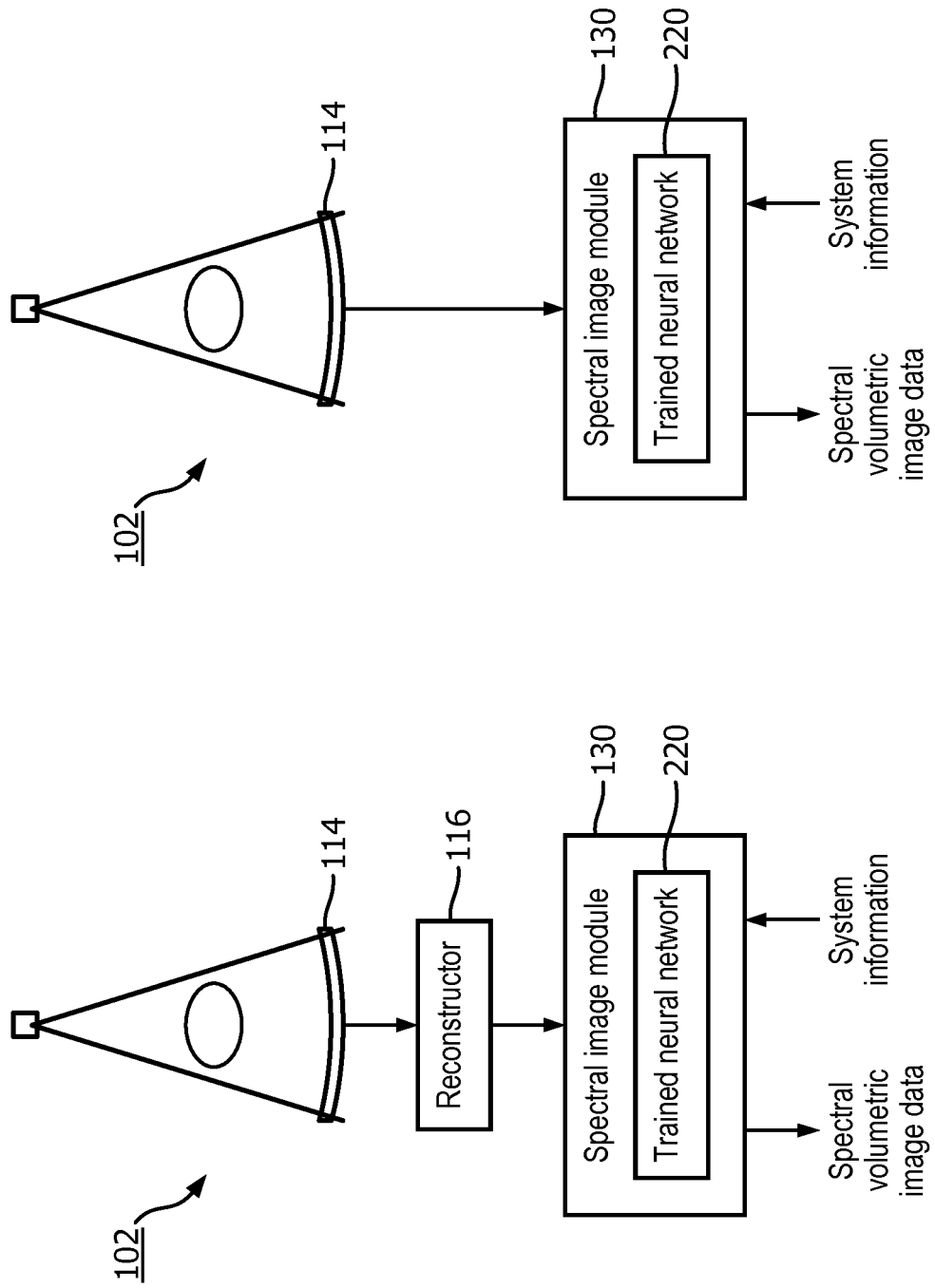

NON-SPECTRAL COMPUTED TOMOGRAPHY (CT) SCANNER CONFIGURED TO GENERATE SPECTRAL VOLUMETRIC IMAGE DATA

FIELD OF THE INVENTION

The following generally relates to imaging and more particularly to a non-spectral computed tomography (CT) scanner configured to generate spectral volumetric image data.

BACKGROUND OF THE INVENTION

A CT scanner generally includes an x-ray tube mounted on a rotatable gantry opposite a detector array. The x-ray tube rotates around an examination region located between the x-ray tube and the detector array, and emits polychromatic radiation that traverses the examination region. The detector array detects radiation that traverses the examination region and generates projection data. The projection data is reconstructed to generate volumetric image data, which can be processed to generate one or more two-dimensional. Generally, corrections (e.g., scatter correction, beam hardening correction) are applied during reconstruction. The images have included pixels represented in terms of gray scale values corresponding to relative radiodensity. These values reflect the attenuation characteristics of the scanned subject and generally show structure such as anatomical structures within the subject.

The detected radiation also includes spectral information as the absorption of the radiation by the subject and/or object is dependent on the energy of the photons traversing therethrough. Such spectral information can provide additional information such as information indicative of the elemental or material composition (e.g., atomic number) of the tissue and/or material of the subject and/or object. Unfortunately, the projection data does not reflect the spectral characteristics as the signal output by the detector array is proportional to the energy fluence integrated over the energy spectrum. Such a CT scanner is also referred to herein as a non-spectral CT scanner. A CT scanner configured for spectral imaging leverages this spectral information to provide further information indicative of elemental or material composition. Such a CT scanner is referred to herein as a spectral CT scanner.

Examples dual-energy spectral configurations include: 1) one x-ray tube emitting x-ray radiation at one energy level and two layers of x-ray detectors respectively detecting lower energy x-rays and higher energy x-rays; 2) one x-ray tube with fast kV-switching and a single-layer detector, and 3) two x-ray tube/single-layer detector pairs angularly offset from each other. Examples of such further information include a low energy high contrast image, an effective Z (atomic number) image, a virtual monochromatic image, a contrast agent quantitative map, a virtual non-contrast image, an electron density image, and/or other spectral information. Unfortunately, the additional detector layer(s), x-ray tubes/detector arrays, and/or kVp switching circuitry increase the overall cost of the imaging system, and the data acquisition, handling, and processing add complexity.

SUMMARY OF THE INVENTION

Aspects described herein address the above-referenced problems and others.

In one aspect, a non-spectral computed tomography scanner includes a radiation source configured to emit x-ray radiation, a detector array configured to detect x-ray radiation and generate non-spectral data, and a memory configured to store a spectral image module that includes computer executable instructions including a neural network trained to produce spectral volumetric image data. The neural network is trained with training spectral volumetric image data and training non-spectral data. The non-spectral computed tomography scanner further includes a processor configured to process the non-spectral data with the trained neural network to produce spectral volumetric image data.

In another aspect, a non-spectral computed tomography scanner includes a radiation source configured to emit x-ray radiation, a detector array configured to detect x-ray radiation and generate non-spectral data, and a memory configured to store a spectral image module that includes computer executable instructions including a neural network trained to produce spectral volumetric image data. The non-spectral computed tomography scanner further includes a processor configured to train the neural network with training spectral volumetric image data and training non-spectral data to generate spectral volumetric image data from the non-spectral data.

In another aspect, a computer readable storage medium is encoded with computer readable instructions, which, when executed by a computer processor of a computing system, causes the computer processor to: emit x-ray radiation with a radiation source, detect emitted x-ray radiation with a detector array and generate a signal indicative thereof, reconstruct the signal and generate non-spectral image data, train a neural network produce spectral volumetric image data, and employ the trained neural network to produce spectral volumetric image data from the generated non-spectral data.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 4 schematically illustrates the system that predicts spectral volumetric image data from non-spectral volumetric image with the neural network trained in FIG. 2.

FIG. 5 schematically illustrates the system that predicts spectral volumetric image data from non-spectral projection data image with the neural network trained in FIG. 3.

DETAILED DESCRIPTION OF EMBODIMENTS

The following describes an approach for generating spectral data from non-spectral projection data and/or non-spectral volumetric image data generated by a non-spectral computed tomography (CT) scanner and system information. In general, non-spectral projection data includes unique spectral information hidden in the data. For example, even though the attenuation along a certain ray path can be the same for both high-Z, low density and low-Z, high density objects, the physical effects, i.e., Compton scatter and photoelectric absorption, can be different with low-Z, high density objects leading to more Compton scatter, and these differences are hidden in the acquired raw projection data. Another example is that there are more beam hardening artifacts for high-Z materials relative to low-Z materials. These differences are minimized or do not show up in the non-spectral volumetric image reconstructed using conventional CT reconstruction due to effective scatter correction and beam-hardening compensation etc.

In one approach described herein, a neural network is trained at least with projection data (which, again, includes unique spectral information), reference spectral data (both data from a same scan and a same CT scanner), and system information. Through training, the neural network learns how to produce spectral data from the non-spectral projection data and the system information. For example, the neural network learns how to produce spectral data corresponding to Compton scatter for high-Z, low density and low-Z, high density objects and photoelectric absorption for high-Z, low density and low-Z, high density objects. Further training can be performed to fine tune the parameters of the neural network such that the neural network can process training non-spectral data and produce spectral data within a given error of training spectral data. Once trained, the trained neural network can process non-spectral projection data from a scan of a patient and system information and produce spectral data for the patient with the neural network. As further described herein, the training data can include non-spectral volumetric image data.

In one instance, the above allows a non-spectral CT scanner to produce not only non-spectral projection data and/or non-spectral volumetric image data, but also spectral projection data and/or spectral volumetric image data. As such, the non-spectral CT scanner can produce spectral projection data and/or spectral volumetric image data without including additional hardware and/or circuitry of a spectral CT scanner, such as multi-layer detector arrays, multiple x-ray tubes/detector array pairs, and/or kVp switching circuitry. Furthermore, it mitigates the data acquisition, handling, and processing complexities of a spectral imaging system.

Figure 1:
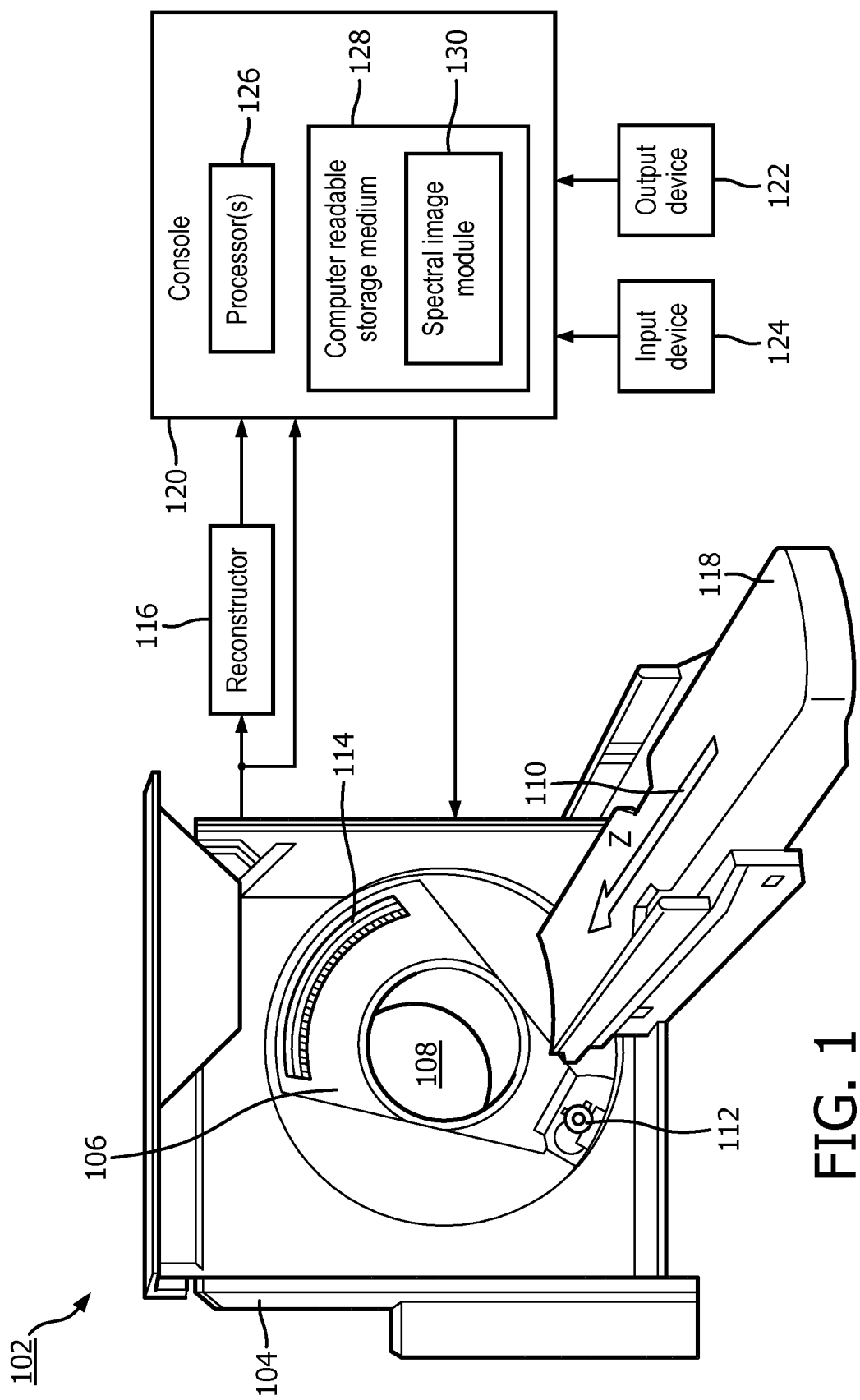
FIG. 1 schematically illustrates an example CT scanner including a spectral image module with a neural network for predicting spectral volumetric image data from non-spectral data.

FIG. 1 schematically illustrates an example non-spectral computed tomography (CT) scanner 102. The CT scanner 102 includes a stationary gantry 104 and a rotating gantry 106, which is rotatably supported by the stationary gantry 104 and rotates around an examination region 108 and a portion of an object or subject therein about a z-axis 110.

A radiation source 112, such as an x-ray tube, is supported by and rotates with the rotating gantry 106 around the examination region 108. The radiation source 112 emits wideband polychromatic x-ray radiation that is collimated to form a generally fan, wedge, or cone shaped x-ray radiation beam that traverses the examination region 108.

A radiation sensitive detector array 114 subtends an angular arc opposite the radiation source 112 across the examination region 108. The detector array 114 includes one or more rows of detectors that are arranged with respect to each other along the z-axis 110 and detects x-ray radiation traversing the examination region 108. The detector array 114 generates non-spectral projection data (line integrals) indicative of the detected radiation.

A reconstructor 116 reconstructs the non-spectral projection data, generating non-spectral volumetric image data. In one instance, the reconstructor 116 applies corrections, before, during and/or after reconstruction. A non-limiting example of a correction is a scatter correction that compensates for scattered radiation, which can degrade image quality, e.g., by adding image artifact. In one instance, this includes subtracting a scatter estimate from the measured data.

A subject support 118, such as a couch, supports a subject or object (e.g., a phantom) in the examination region 108. The subject support 118 is movable in coordination with performing an imaging procedure so as to guide the subject or object with respect to the examination region 108 for loading, scanning, and/or unloading the subject or object.

An operator console 120 includes a human readable output device 122 such as a display monitor, a filmer, etc. and an input device 124 such as a keyboard, mouse, etc. The console 120 further includes a processor 126 (e.g., a central processing unit (CPU), a microprocessor, etc.) and computer readable storage medium 128 (which excludes transitory medium) such as physical memory. In the illustrated embodiment, the computer readable storage medium 128 includes a spectral image module 130.

The spectral image module 130 includes instructions configured to process the non-spectral projection data and/or the non-spectral volumetric image data from the detector array 114 and/or the reconstructor 116 to predict spectral volumetric image data such as a low energy high contrast image, an effective Z (atomic number) image, a virtual monochromatic image, a contrast agent quantitative map, a virtual non-contrast image, an electron density image, and/or other spectral image. As described in greater detail below, the instructions include a neural network trained with 1) spectral data, 2) one from a group consisting of non-spectral projection data, fully corrected non-spectral volumetric image data, and uncorrected/partially corrected non-spectral volumetric image data, and 3) system information.

With the configuration described herein, the non-spectral imaging system 102 directly reconstructs spectral volumetric image data from non-spectral projection data or non-spectral volumetric image data and system information. As such, the spectral image module 130 mitigates employing multi-layer detector arrays, multiple x-ray tubes/detector array pairs, and/or kVp switching circuitry to produce spectral volumetric image data. This mitigates an increase in overall system cost associated with multi-layer detector arrays, multiple x-ray tubes/detector pairs, and/or kVp switching circuitry. Furthermore, it mitigates the data acquisition, handling, and processing complexities of a spectral imaging system.

Figure 2:
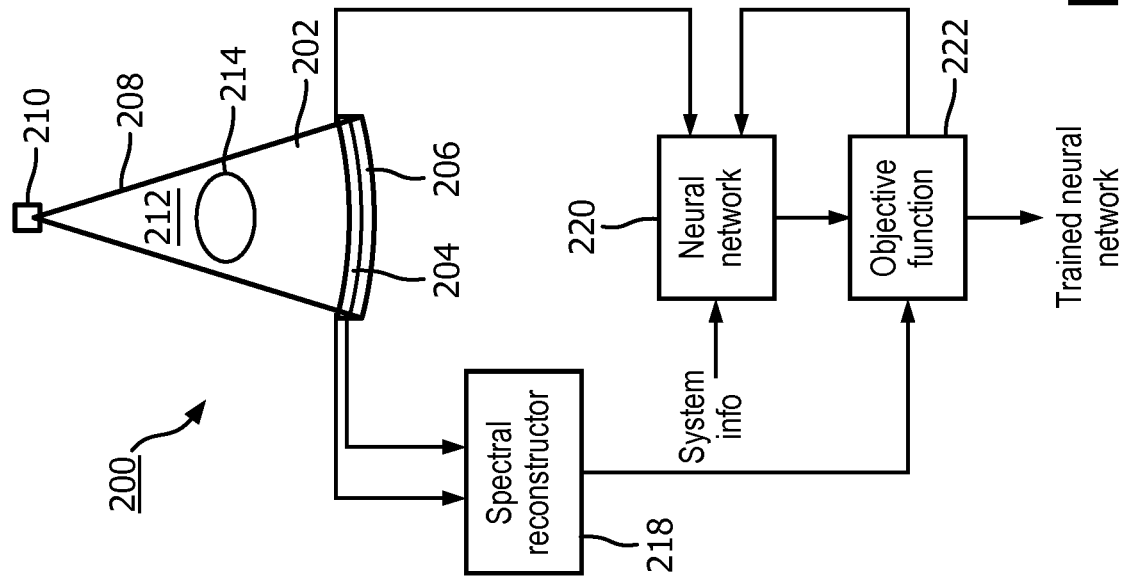
FIG. 2 schematically illustrates an example of training the neural network with spectral volumetric image data and non-spectral (corrected or uncorrected) volumetric image data.

FIG. 2 schematically illustrates example training of the neural network of the spectral image module 130.

In this example, the neural network is trained with data generated by a CT scanner 200 configured with a dual layer detector array 202, which includes a first layer 204 and a second layer 206. A non-limiting example of a multi-layer detector array is described in U.S. Pat. No. 7,968,853 B2, filed Apr. 10, 2006, and entitled "Double decker detector for spectral CT," which is incorporated herein by reference in its entirety. A beam 208 generated by an x-ray tube 210 traverses an examination region 212 and an object or subject 214 disposed therein and is detected by the dual layer detector array 202.

The first layer 204 produces first projection data, which is processed by a non-spectral reconstructor 216, which employs a non-spectral reconstruction algorithm to produce non-spectral volumetric image data. In this example, the non-spectral reconstructor 216 applies a beam hardening correction, a scatter correction and/or one or more other corrections, and the resulting non-spectral volumetric image data is referred to as corrected non-spectral volumetric image data.

The second layer 206 produces second projection data, which is provided to a spectral reconstructor 218 along with the first projection data. The energy spectrum of the first and second projection data is different, with an energy spectrum of the second projection data being higher than an energy spectrum of the first projection data. The spectral reconstructor 218 employs one or more spectral algorithms to produce one or more sets of spectral volumetric image data.

A neural network 220 is trained with the one or more sets of spectral volumetric image data, system information, and the non-spectral volumetric image data. For example, where a set of spectral volumetric image data includes a low energy high contrast image, the neural network is trained to predict a low energy high contrast image from the non-spectral volumetric image data and the system information, where a set of spectral volumetric image data includes an effective Z image, the neural network is trained to predict an effective Z image from the non-spectral volumetric image data and the system information, etc.

In one instance, the neural network 220 is built as follows. A reconstructed image I from a specific system S (the system 200 in this example) can be considered to be a summation of an artifact free image $I_{artifact-free}$ and an artifact image $I_{artifact}$, or $I = I_{artifact-free} + I_{artifact-free}$. Each voxel in the artifact free image can be further decomposed into photo component and scatter component, which are not system specific ($I_{artifact-free} = \alpha\mu_p + \beta\mu_s$). Artifacts, such as beam hardening and scatter artifacts, are a function of the photo component and the scatter component, given a fixed input x-ray spectra, system geometry and detector configuration ($I_{artifact} = (\alpha\mu, \beta\mu_s, S)$. Artifacts in the image can be detected given a specific system configuration, e.g., using a neural network to detect metal artifacts and scatter artifacts).

With function f known, α and β can be solved by combining $I_{artifact-free} = \alpha\mu_p + \beta\mu_s$ and $I_{artifact} = (\alpha\mu, \beta\mu_s, S)$. The neural network 220 is trained to fit the function f such that spectral info (α and β), which are the concentrations of scatter and photo containing the spectral information, from the non-spectral volumetric image data can be identified with image artifacts. The specific system configuration information includes detector information (e.g., detector position, detector response, anti-scatter grid geometry and materials), radiation source information (e.g., source position, spectra distribution), and other system specific information (e.g., iso-center, collimation, etc.).

Trainable parameters of the neural network 220 are then updated and converge through a number of iterations using an objective function 222. The objective function 222, in one instance, includes a mathematical function that minimizes an error between the training spectral and system information and non-spectral volumetric image data, e.g., based on a mean squared and/or other difference therebetween. In this instance, the parameters are updated until the error falls below of predetermined threshold. Other stopping criteria include a predetermined number of iterations, a predetermined time duration, etc.

In one instance, the objective function 222 is implemented as a cost function L(w), e.g., as shown in EQUATION 1:

$$L(w) = \sum_j \|T(NSI, Sinfo; w)_j - SI_j\|_2^2 + \lambda_2 \sum_k \|w_k\|_2^2, \quad \text{EQUATION 1}$$

where NSI is a jth set of training non-spectral volumetric image data, Sinfo is a jth set of system specific information, SI is a jth set of training spectral volumetric image data, and T represents a transformation that transforms the NSI and Sinfo into SI with trainable parameters w, $\lambda_2 \Sigma_k \|w_k\|2/2$ represents a regularization term that drives the equation towards small parameters w, $\mu_2$ represents a hyperparameter, and k represents an index. By minimizing the cost function, function T parameterized by w is resolved iteratively.

In this example, as discussed above, the non-spectral reconstructor 216 applies at least a scatter and/or beam hardening correction. Such corrections reduce or remove spectral information. For example, and as described above, the photo-electric effect and Compton scatter difference between a low-Z, high density structure and a high-Z, low density structure is reflected in the non-spectral projection data. In general, the projection data for the low-Z, high density structure will include more scatters. A scatter correction can remove or reduce this difference. In addition, there are more beam hardening artifacts for high Z materials than low Z materials. A beam hardening correction can remove or reduce this difference. In a variation, corrections that remove spectral information, such as a scatter correction and/or beam hardening, are omitted. The resulting data is referred to herein as partially corrected (some of the corrections are omitted) or uncorrected (all corrections are omitted) non-spectral volumetric image data.

Figure 3:
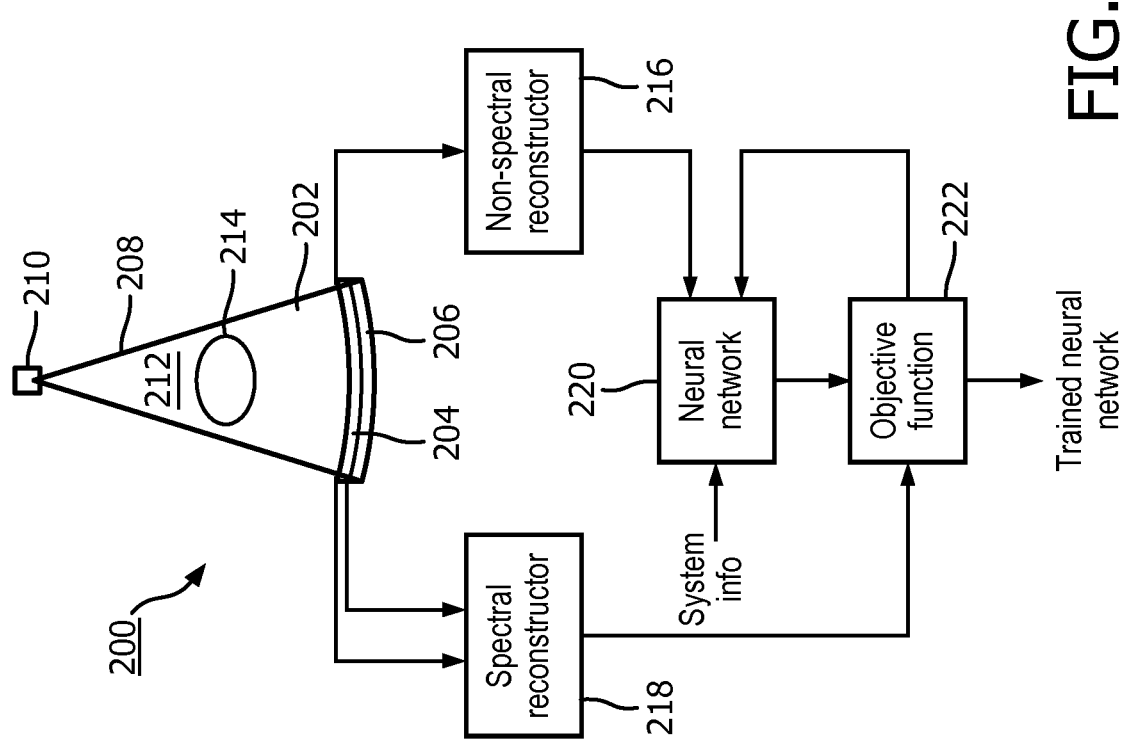
FIG. 3 schematically illustrates an example of training the neural network with spectral volumetric image data and non-spectral projection data.

FIG. 3 schematically illustrates another example training of the neural network of the spectral image module 130. In this example, the neural network 220 is trained with data generated by the same CT scanner 200 as that described in connection with FIG. 2. However, the neural network 220 is trained with the non-spectral projection data from the first layer 204 and not the non-spectral volumetric image data from the non-spectral reconstructor 216.

The neural network 220 trained using the examples described in connection with FIGS. 2 and 3 are well-suited for a non-spectral CT scanner including a detector array that is similar to the first layer 204 of the spectral CT scanner 200. However, the trained neural network 220 can be employed with other detector arrays. In these instances, the neural network 220 training may also include scanner information such as detector geometry and radiation detection characteristics.

FIGS. 2 and 3 describe examples where the neural network is trained with data generated by a CT scanner (the CT scanner 200) configured with a dual-layer detector array 202. In a variation, the neural network is trained with data generated by a spectral CT scanner configured with more than two layers. In yet another variation, the spectral CT scanner is configured with photon counting (direct conversion) detectors, and the neural network is trained with data generated therefrom.

In another variation, the neural network is trained with data generated by a spectral CT scanner configured with multiple X-ray tubes. In this instance, the non-spectral projection data is for one of the x-ray tube/detector array pairs. In another variation, the neural network is trained with data generated by a spectral CT scanner configured with kVp switching circuitry. In this instance, the non-spectral projection data is for one of the kVp's. An example of a system configured with multiple X-ray tubes and/or kVp switching circuitry is described in U.S. Pat. No. 8,442,184 B2, filed Jun. 1, 2009, and entitled "Spectral CT," which is incorporated herein by reference in its entirety.

FIG. 4 schematically illustrates the non-spectral CT scanner 102 where the spectral image module 130 predicts, using the trained neural network 220 of FIG. 2, spectral volumetric image data from non-spectral volumetric image data reconstructed with the reconstructor 116 and information about the non-spectral CT scanner 102 such as information about the detector array 114, the radiation source 112, such as system geometry and physics information (e.g., x-ray spectra and detector response), and/or other system specific information. FIG. 5 schematically illustrates the system 102 where the spectral image module 130 predicts, using the trained neural network of FIG. 3, spectral volumetric image data from non-spectral projection data generated by the detector array 114 and the information about the non-spectral CT scanner 102.

Figure 6:
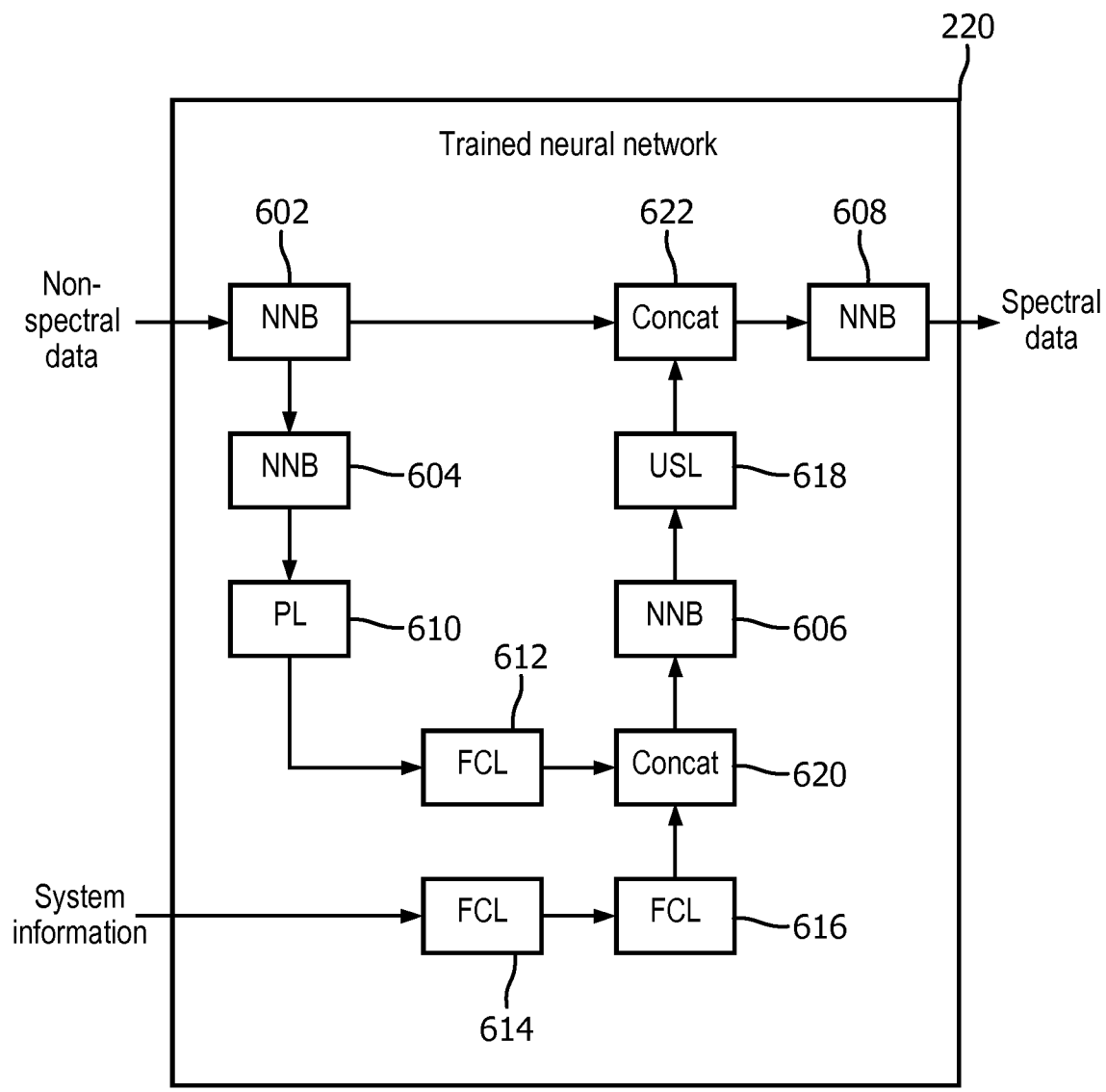
FIG. 6 schematically illustrates an example neural network.

FIG. 6 schematically illustrates an example of a suitable neural network 220. The input includes the non-spectral data (e.g., projection data or volumetric image data). In one instance, the entire 3D non-spectral data is processed. In another instance, a sub-set thereof (e.g., a slice, a slice and neighboring slices, a slice and multiplanar reformatted (MPR) slices, etc. for image data) is processed. It is to be understood that this example is illustrative, and other neural networks are contemplated herein, including deeper neural networks. The input further includes the system information, e.g., input as a 1D vector. The output is spectral data.

In this example, the neural network 220 is a three-dimensional (3-D) convolutional neural network with neural network blocks (NNB) 602, 604, 606 and 608. Each of the blocks 602, 604, 606 and 608 can contain one or more layers, each layer including one or more convolutional layers, batch normalization layers and rectified linear units. The neural network further includes a pooling layer (PL) 610, one or more fully connected layers (FCL) 612, 614 and 616, an up-sampling layer (USL) 618, and at least two concatenation layers (concat) 620 and 622. The input is the non-spectral volumetric image data or the non-spectral projection data and the system information, and the output is the predicted spectral volumetric image data.

In general, the convolutional layers include convolutional neurons that apply a convolution operation to the input. The batch normalization layers normalize the output of the convolutional layers before the output is processed by the rectified linear units. The rectified linear units apply a non-linear activation function to its input. The pooling layer 610 down-samples its input. The output of the block 610 is vectorized. The fully connected layers 612-616 combine features learned by the previous layers. The concatenation layer 620 concatenates the output of fully connected layers 612 and 616. In one instance this includes concatenating the vectorized non-spectral data and the system information vector along channels, and reshaping the vectors. The up-sampling layer 618 up-samples its input back to the original or other size. The concatenation layer 622 concatenates the outputs of the block 602 and the up-sampling layer 618. The block 608 outputs the spectral data.

Examples of convolution network are further described in Gouk, et al., "Fast Sliding Window Classification with Convolutional Neural Networks," IVNVZ '14 Proceedings of the 29th International Conference on Image and Vision Computing New Zealand, Pages 114-118, Nov. 19-21, 2014, "Fully convolutional networks for semantic segmentation," Proceedings of the IEEE Conference on Computer Vision and Pattern Recognition, 2015, and Ronneberger, et al., "U-Net: Convolution Networks for Biomedical Image Segmentation," Medical Image Computing and Computer-Assisted Intervention (MICCAI), Springer, LNCS, Vol. 9351: 234-241, 2015.

Figure 7:
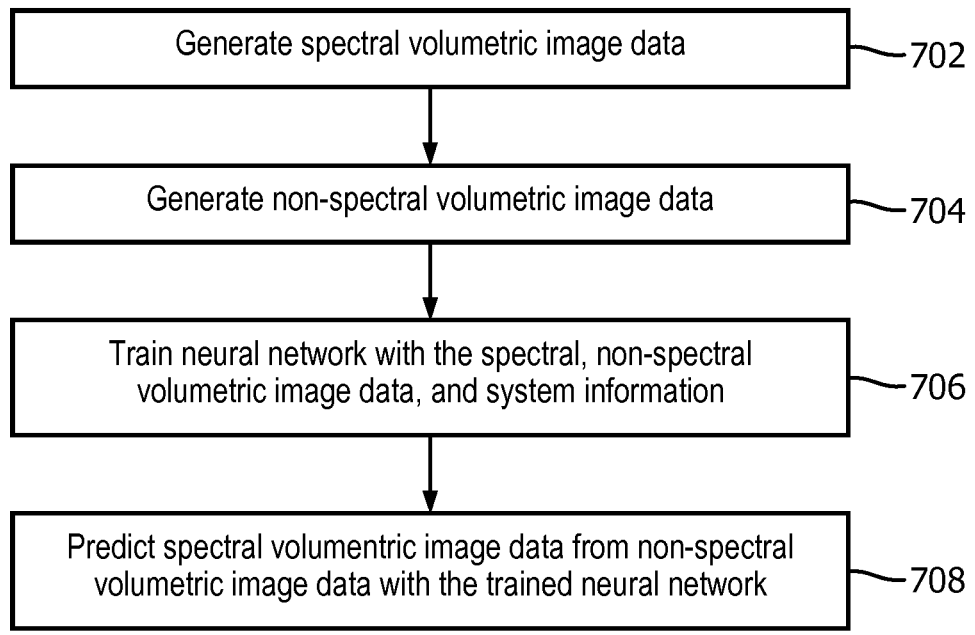
FIG. 7 illustrates an example method in accordance with FIGS. 1, 2 and 4.

FIG. 7 illustrates an example method in accordance with an embodiment herein.

It is to be appreciated that the ordering of the acts in the method is not limiting. As such, other orderings are contemplated herein. In addition, one or more acts may be omitted, and/or one or more additional acts may be included.

At 702, spectral volumetric image data is generated with a spectral imaging system, as described herein and/or otherwise.

At 704, non-spectral volumetric image data is generated with the same spectral imaging system, as described herein and/or otherwise.

At 706, the spectral volumetric image data, the non-spectral volumetric image data and system information are employed to train a neural network to predict spectral volumetric image data from the non-spectral volumetric image data.

At 708, the trained neural network is employed to predict spectral volumetric image data from non-spectral volumetric image data from a non-spectral scanner and system information for that non-spectral scanner.

Figure 8:
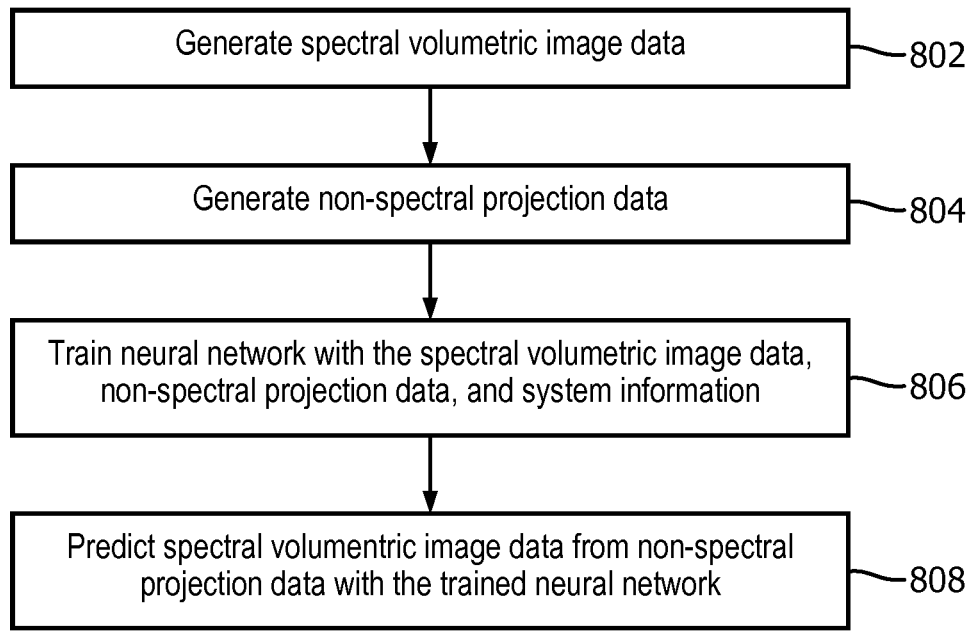
FIG. 8 illustrates an example method in accordance with FIGS. 1, 3 and 5.

FIG. 8 illustrates an example method in accordance with an embodiment herein.

It is to be appreciated that the ordering of the acts in the method is not limiting. As such, other orderings are contemplated herein. In addition, one or more acts may be omitted, and/or one or more additional acts may be included.

At 802, spectral volumetric image data is generated with a spectral imaging system, as described herein and/or otherwise.

At 804, non-spectral projection data is generated with the same spectral imaging system, as described herein and/or otherwise.

At 806, the spectral volumetric image data, the non-spectral projection data are employed and system information to train a neural network to predict spectral volumetric image data from the non-spectral projection data.

At 808, the trained neural network is employed to predict spectral volumetric image data from non-spectral projection data from a non-spectral scanner and system information for that non-spectral scanner.

The spectral images include a single type or multiples types of spectral images. For example, in one instance the spectral images include effective low keV images (e.g., for maximum tissue contrast). In another instance, the spectral images include effective Z images. In yet another instance, the spectral images include both effective low keV images and effective Z images. In still another instance, the spectral images include one or more other types of spectral images.

Where the spectral images include multiples types of spectral images, a different neural network can be trained for each of the multiples types. In another instance, a combined neural network is trained for at least two different types of spectral images. The multiple and/or combined trained neural networks are employed to predict one or more spectral volumetric image data sets for one or more types of spectral images from non-spectral data. This includes predicting effective low keV images and effective Z images in the above example.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A non-spectral computed tomography scanner, comprising:
    a radiation source configured to emit x-ray radiation;
    a detector array configured to detect the x-ray radiation and generate non-spectral data;
    a memory configured to store a spectral image module that includes a neural network trained with training spectral volumetric image data and training non-spectral data; and
    a processor configured to process the non-spectral data with the trained neural network to produce spectral volumetric image data.

2. The scanner of claim 1, wherein the neural network is further trained with scanner geometry and physics information.

3. The scanner of claim 1, wherein the non-spectral data includes non-spectral projection data, and the processor is configured to process the non-spectral projection data using the trained neural network to produce the spectral volumetric image data.

4. The scanner of claim 3, wherein the training non-spectral data includes training non-spectral projection data.

5. The scanner of claim 4, wherein the non-spectral data includes non-spectral volumetric image data, and the processor is configured to process the non-spectral volumetric image data using the trained neural network to produce the spectral volumetric image data.

6. The scanner of claim 1, wherein the training non-spectral data includes training non-spectral volumetric image data.

7. The scanner of claim 6, wherein the non-spectral volumetric image data is uncorrected spectral volumetric image data.

8. The scanner of claim 6, wherein the non-spectral volumetric image data is partially corrected spectral volumetric image data, which is not corrected at least for beam hardening and scatter radiation.

9. The scanner of claim 4, wherein the neural network is trained to minimize a difference between the spectral volumetric image data generated by the neural network and the training non-spectral data.

10. The scanner of claim 6, wherein the non-spectral volumetric image data is corrected spectral volumetric image data.

11. A non-spectral computed tomography scanner, comprising:
    a radiation source configured to emit x-ray radiation;
    a detector array configured to detect the x-ray radiation and generate non-spectral data;
    a memory configured to store a spectral image module that includes a neural network trained; and
    a processor configured to train the neural network with training spectral volumetric image data and training non-spectral data to generate spectral volumetric image data from the non-spectral data.

12. The scanner of claim 11, wherein the training non-spectral data includes training non-spectral projection data.

13. The scanner of claim 12, wherein the neural network is trained to minimize a difference between the spectral volumetric image data generated by the neural network and the training non-spectral projection data.

14. The scanner of claim 12, wherein the non-spectral data includes non-spectral projection data, and the processor is further configured to process the non-spectral projection data with the trained neural network to produce spectral data.

15. The scanner of claim 11, wherein the training non-spectral data includes training non-spectral volumetric image data.

16. The scanner of claim 15, wherein the neural network is trained to minimize a difference between the spectral volumetric image data generated by the neural network and the training non-spectral volumetric image data.

17. A non-transitory computer readable storage medium encoded with computer readable instructions, which, when executed by a processor of a computing system, cause the processor to:
    emit x-ray radiation with a radiation source;
    detect the emitted x-ray radiation and generate a signal indicative of the emitted x-ray radiation;
    reconstruct the signal and generate non-spectral volumetric image data; and
    deploy a neural network trained to produce spectral volumetric image data from the generated non-spectral volumetric image data.

18. The non-transitory computer readable storage medium of claim 17, wherein the generated non-spectral volumetric image data is obtained from non-spectral projection data generated by a non-spectral computed tomography scanner.

19. A method used in a non-spectral computed tomography scanner, the method comprising:
    emitting x-ray radiation;
    detecting the emitted x-ray radiation;
    generating non-spectral data indicative of the emitted x-ray radiation;

storing a spectral image module that includes a neural network trained with training spectral volumetric image data and training non-spectral data; and processing the non-spectral data with the trained neural network to produce spectral volumetric image data.

\* \* \* \* \*